United States Patent
Szarvas et al.

(10) Patent No.: US 8,252,943 B2
(45) Date of Patent: Aug. 28, 2012

(54) METHOD FOR THE PRODUCTION OF COMPOUNDS WITH QUATERNARY SP²-HYBRIDISED NITROGEN ATOMS

(75) Inventors: Laszlo Szarvas, Ludwigshafen (DE); Matthias Maase, Speyer (DE); Klemens Massonne, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 1288 days.

(21) Appl. No.: 10/591,114

(22) PCT Filed: Mar. 3, 2005

(86) PCT No.: PCT/EP2005/002253
§ 371 (c)(1),
(2), (4) Date: Aug. 31, 2006

(87) PCT Pub. No.: WO2005/085207
PCT Pub. Date: Sep. 15, 2005

(65) Prior Publication Data
US 2007/0142642 A1 Jun. 21, 2007

(30) Foreign Application Priority Data
Mar. 4, 2004 (DE) .......................... 10 2004 010 662

(51) Int. Cl.
*C07D 233/54* (2006.01)
(52) U.S. Cl. .................................................. 548/335.1
(58) Field of Classification Search ................ 548/335.1
See application file for complete search history.

(56) References Cited

U.S. PATENT DOCUMENTS

| 3,371,117 A | 2/1968 | Campbell et al. |
| 6,881,698 B2 | 4/2005 | Bonnet et al. |
| 2005/0070717 A1 | 3/2005 | Wasserscheid et al. |

FOREIGN PATENT DOCUMENTS

| DE | 15 43 747 | 12/1969 |
| EP | 1 182 196 | 2/2002 |
| EP | 1 182 197 | 2/2002 |
| EP | 1182197 A1 * | 2/2002 |
| JP | 200016995 A | 8/2001 |
| JP | 2003313170 A | 11/2003 |
| WO | WO-00/32658 | 6/2000 |
| WO | WO-01/81353 | 11/2001 |
| WO | WO-02/094883 | 11/2002 |
| WO | WO-03/074494 | 9/2003 |

OTHER PUBLICATIONS

Wilkes, J.S. et al., "Air and Water Stable 1-Ethyl-3-methylimidazolium Based Ionic Liquids", J. Chem. Soc., Chem. Commun. (1992), pp. 965-967.
Wasserscheid, P. et al., "1-*n*-Butyl-3-methylimidazolium ([bmim]) octylsulfate—An Even 'Greener' Ionic Liquid", Green Chemistry, Royal Society of Chemistry, Cambridge, GB, 4:4 (2002), pp. 400-404.

* cited by examiner

*Primary Examiner* — Joseph Kosack
(74) *Attorney, Agent, or Firm* — Connolly Bove Lodge & Hutz LLP

(57) ABSTRACT

Process for preparing ionic compounds comprising cations containing quaternary sp²-hybridized nitrogen atoms, which comprises reacting compounds containing a double-bonded nitrogen atom with a dialkyl sulfate with participation of both alkyl groups of the dialkyl sulfate and, if appropriate, subjecting the resulting ionic compound containing sulfate anions to an anion exchange.

12 Claims, No Drawings

METHOD FOR THE PRODUCTION OF COMPOUNDS WITH QUATERNARY SP²-HYBRIDISED NITROGEN ATOMS

RELATED APPLICATIONS

This application is a national stage application (under 35 U.S.C. 371) of PCT/EP2005/002253 filed Mar. 3, 2005, which claims benefit to German application 10 2004 010 662.2 filed Mar. 4, 2004.

The present invention relates to a process for preparing ionic compounds comprising cations containing quaternary sp²-hybridized nitrogen atoms, which comprises reacting compounds containing a double-bonded nitrogen atom with a dialkyl sulfate at elevated temperature with participation of both alkyl groups of the dialkyl sulfate and, if appropriate, subjecting the resulting ionic compound containing sulfate anions to an anion exchange.

Salts, i.e. heteropolar compounds made up of cations and anions, generally have very high melting points which are as a rule greater than 500° C. In addition, classical melts of pure salts or eutectic mixtures generally have a high viscosity. Completely different behavior is displayed by ionic liquids. For the purposes of the present invention, ionic liquids are liquids which consist exclusively of ions and are liquid at room temperature or slightly elevated temperature (<100° C.). Owing to their particular properties, such ionic liquids have found wide use. Thus, for example, they serve as solvents for reactions catalyzed by transition metals and as extractants for separation of materials. As "designer solvents", ionic liquids are expected to have a great development potential in the future, with it being assumed that selective exchange of both the cationic part and the anionic part will make it possible to prepare as yet unknown solvents tailored for a particular purpose. There is therefore a great need for processes suitable for preparing ionic liquids.

In J. Chem. Soc., Chem. Commun., 1992, pp. 965-967, J. S. Wilkes and M. J. Zaworotko describe ionic liquids based on the 1-ethyl-3-methylimidazolium cation which are stable to air and water and are therefore suitable for many applications. Starting from the iodide compound, it is possible to prepare further anions, e.g. the sulfate in the form of its monohydrate, by anion exchange with the corresponding silver salts.

The use of ionic compounds containing halide anions as precursors for ionic liquids having different anions is problematic. Thus, ionic liquids have to meet specific purity requirements, especially for use as solvents in transition metal catalysis. Traces of halide ions, in particular chloride, bromide and iodide, act as catalyst poisons for many transition metal catalysts. Owing to their nonvolatile nature, inorganic liquids cannot be purified by distillation like organic solvents. Selective exchange of halide ions for other anions or selective removal of residual amounts of halide ions present from ionic liquids is possible by use of anion exchangers, but due to the high cost incurred it is economically unattractive. A synthesis of ionic liquids which is halide-free from the beginning is therefore desirable.

EP-A-1 182 196 describes a process for preparing ionic liquids, in which the amines, phosphines, imidazoles, pyridines, triazoles or pyrazoles on which the cation is based are alkylated by means of a dialkyl sulfate, giving salts of the corresponding monoalkylsulfate anions which are subsequently subjected to an anion exchange with metal salts.

WO 00/32658 describes ionic liquids and their use for preparing polyisoolefins having a high molecular weight.

WO 03/074494 describes halogen-free ionic liquids based on anions of the formula $[R'—O—SO_3]^-$ or $[R'—SO_3]^-$, where R' is a group of the general formula $R^5—[X(—CH_2—)_n]_m$, in which n is a number from 1 to 12, m is a number from 1 to 400, X is oxygen, sulfur or a group of the general formula $—O—Si(CH_3)_2—O—$, $—O—Si(CH_2CH_3)_2—O—$, $—O—Si(OCH_3)_2—O—$ or $—O—Si(O—CH_2CH_3)_2—O—$ and $R^5$ is a linear or branched, saturated or unsaturated, aliphatic or alicyclic alkyl group which may be unfunctionalized or be functionalized by one or more groups Y and has from 1 to 36 carbon atoms, where Y is a —OH, —OR", —COOH, —COOR", —NH₂, —SO₄, —F, —Cl, —Br, —I or —CH group in which R" is a branched or linear hydrocarbon chain having from 1 to 12 carbon atoms. They are prepared from pyridine-SO₃ complexes and ethers of the formula R'—OH.

It is known that amines can be alkylated by dialkyl sulfates, but generally only one alkyl group of the dialkyl sulfate is utilized, so that the corresponding monoalkylsulfate salts result. DE-A-15 43 747 describes a process for the direct preparation of a bisquaternary ammonium salt from a dialkyl sulfate ester and a trialkylamine by reaction at a temperature in the range from 0 to 400° C. and a pressure sufficient to prevent vaporization of the amine. Since hydrolysis of the sulfate ester takes place at elevated temperatures, this document teaches carrying out the reaction in two stages, with one alkyl group of the sulfate ester in the alkylation initially participating at a low temperature in the range from about 0 to 50° C. and then the second alkyl group in a second step at an elevated temperature in the range from about 50 to 400° C.

It is an object of the present invention to provide a simple and thus economical process for preparing ionic compounds which are suitable as ionic liquids or are suitable for preparing ionic liquids. In particular, the process should be suitable for preparing ionic liquids which are substantially free of halides, especially free of chloride, bromide and iodide.

It has surprisingly been found that this object is achieved by a process which comprises reacting a compound containing a double-bonded (sp²-hybridized) nitrogen atom with a dialkyl sulfate at elevated temperatures to give an ionic compound containing a sulfate anion as anion component and, if appropriate, subsequently exchanging the sulfate anion for a different anion.

The invention accordingly provides processes for preparing an ionic compound comprising at least one cation containing a quaternary sp²-hybridized nitrogen atom, which comprises a) reacting a compound containing a double-bonded nitrogen atom with a dialkyl sulfate with participation of both alkyl groups of the dialkyl sulfate to give an ionic compound containing sulfate anions, and b) if appropriate, subjecting the ionic compound obtained in step a) to an anion exchange.

It has surprisingly been found that compounds which contain at least one double-bonded nitrogen atom can be quaternized by alkyl sulfates with participation of both alkyl groups. This advantageously gives ionic compounds which have doubly negatively charged sulfate anions instead of singly negatively charged alkylsulfate anions as anion component. In this way, the alkyl group equivalents of the dialkyl sulfate can firstly be effectively utilized and, secondly, the sulfate compounds obtained are good intermediates for the preparation of halide-free ionic liquids. The hydrolysis which is described in the prior art as a disadvantage of double alkylation using dialkyl sulfates is advantageously not observed in the process of the invention. The fact that compounds containing at least one double-bonded nitrogen atom are suitable for the alkylation according to the invention with participation of both alkyl groups of a dialkyl sulfate is surprising because the nitrogen atom is sp²-hybridized in these compounds and these compounds are weaker bases than amines in which the nitrogen atom is sp³-hybridized.

For the purposes of the present invention, compounds containing at least one double-bonded nitrogen atom include resonance-stabilized compounds, e.g. aromatic compounds, in which only individual resonance structures (mesomeric limiting structures) have a double bond to the nitrogen atom.

For the purpose of explaining the present invention, the expression "alkyl" encompasses straight-chain and branched alkyl groups. It preferably refers to straight-chain or branched $C_1$-$C_{20}$-alkyl, preferably $C_1$-$C_{10}$-alkyl groups, particularly preferably $C_1$-$C_8$-alkyl groups and very particularly preferably $C_1$-$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also encompasses substituted alkyl groups which generally have 1, 2, 3, 4 or 5 substituents, preferably 1, 2 or 3 substituents and particularly preferably 1 substituent. These are, for example, selected from among cycloalkyl, aryl, hetaryl, halogen, amino, alkoxycarbonyl, acyl, nitro, aminocarbonyl, alkylaminocarbonyl, dialkylaminocarbonyl, alkylcarbonylamino, carboxylate and sulfonate.

The expression "alkylene" as used for the purposes of the present invention refers to straight-chain or branched alkanediyl groups which preferably have from 1 to 5 carbon atoms.

The expression "cycloalkyl" as used for the purposes of the present invention encompasses both unsubstituted and substituted cycloalkyl groups, preferably $C_5$-$C_8$-cycloalkyl groups, e.g. cyclopentyl, cyclohexyl or cycloheptyl. If they are substituted, these can generally bear 1, 2, 3, 4 or 5 substituents, preferably 1, 2 or 3 substituents. These substituents are, for example, selected from among alkyl and the substituents mentioned above for substituted alkyl groups.

The expression "heterocycloalkyl" as used for the purposes of the present invention encompasses saturated, cycloaliphatic groups which generally have from 4 to 7, preferably 5 or 6 ring atoms and in which 1, 2, 3 or 4 of the ring carbons are replaced by heteroatoms selected from among the elements oxygen, nitrogen and sulfur and which may optionally be substituted. If they are substituted, these heterocycloaliphatic groups can bear, for example, 1, 2 or 3 substituents. These substituents are, for example, selected from among alkyl and the substituents mentioned above for substituted alkyl groups. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

The expression "aryl" as used for the purposes of the present invention encompasses both unsubstituted and substituted aryl groups, and preferably refers to phenyl, tolyl, xylyl, mesityl, naphthyl, fluorenyl, anthracenyl, phenanthrenyl or naphthacenyl, particularly preferably phenyl or naphthyl. If they are substituted, these aryl groups can generally bear 1, 2, 3, 4 or 5 substituents, preferably 1, 2 or 3 substituents. The substituents are, for example, selected from among alkyl and the substituents mentioned above for substituted alkyl groups.

The expression "hetaryl" as used for the purposes of the present invention encompasses unsubstituted or substituted, heterocycloaromatic groups, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl. If they are substituted, these heterocyclyl aromatic groups can generally have 1, 2 or 3 substituents. These substituents are, for example, selected from among alkyl and the substituents mentioned above for substituted alkyl groups.

For the purposes of the present invention, carboxylate and sulfonate are preferably derivatives of a carboxylic acid function or a sulfonic acid function, in particular a metal carboxylate or sulfonate, a carboxylic ester or sulfonic ester function or a carboxamide or sulfonamide function. They include, for example, esters with $C_1$-$C_4$-alkanols such as methanol, ethanol, n-propanol, isopropanol, n-butanol, sec-butanol and tert-butanol.

The above explanations of the expressions "alkyl", "cycloalkyl", "aryl", "heterocycloalkyl" and "hetaryl" apply analogously to the expressions "alkoxy", "cycloalkoxy", "aryloxy", "heterocycloalkoxy" and "hetaryloxy".

The expression "acyl" as used for the purposes of the present invention refers to alkanoyl or aroyl groups which generally have from 2 to 11, preferably from 2 to 8, carbon atoms, for example the acetyl, propanoyl, butanoyl, pentanoyl, hexanoyl, heptanoyl, 2-ethylhexanoyl, 2-propylheptanoyl, benzoyl or naphthoyl group.

The groups $NE^1E^2$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine and iodine, preferably fluorine, chlorine and bromine.

$M^+$ is a cation equivalent, i.e. a monovalent cation or the fraction of a polyvalent cation corresponding to a single positive charge. The cation $M^+$ serves merely as counterion to balance the charge of negatively charged substituent groups such as $COO^-$ or the sulfonate group and can in principle be chosen at will. Preference is therefore given to using alkali metal ions, in particular $Na^+$, $K^+$, $Li^+$ ions, or onium ions such as ammonium, monoalkylammonium, dialkylammonium, trialkylammonium, tetraalkylammonium, phosphonium, tetraalkylphosphonium or tetraarylphosphonium ions An analogous situation applies to the anion equivalent $A^-$ which serves merely as counterion for positively charged substituent groups such as the ammonium groups and can be chosen at will among monovalent anions and the fractions of a polyvalent anion corresponding to a single negative charge, with preference generally being given to anions other than halide ions.

The process of the invention is suitable quite generally for preparing ionic compounds of the formula I $$bB^{m+}xX^{n-} \qquad (I)$$

where $B^{m+}$ is an m-valent cation containing at least one quaternary sp²-hybridized nitrogen atom, $X^{n-}$ is an n-valent anion, b and x are integers $\geq 1$, with the proviso that (b times m)=(x times n).

Compounds of this type include compounds of the formulae $B^+X^-$, $B^{m+}X^{m-}$, $nB^+X^{n-}$ and $B^{m+}mX^-$, where m and n are integers >1.

The anion component $X^{n-}$ is preferably an anion other than Cl⁻, Br⁻, I⁻ and monoalkylsulfates. The anions $X^{n-}$ are preferably selected from among sulfate ($SO_4^{2-}$), hydrogensulfate ($HSO_4^-$), nitrite ($NO_2^-$), nitrate ($NO_3^-$), cyanide ($CN^-$), cyanate ($OCN^-$), isocyanate ($NCO^-$), thiocyanate ($SCN^-$), isothiocyanate ($NCS^-$), phosphate ($PO_4^{3-}$), hydrogenphosphate ($HPO_4^{2-}$), dihydrogenphosphate ($H_2PO_4^-$), primary phosphite ($H_2PO_3^-$), secondary phosphite ($HPO_3^{2-}$), orthoborate ($BO_3^{3-}$), metaborate (($BO_2)_3^{3-}$), tetrafluoroborate ($[BF_4]^-$), tetrachloroborate ($[BCl_4]^-$), tetraphenylborate ($[B(C_6H_5)_4]^-$), hexafluorophosphate ($[PF_6]^-$), hexafluoroantimonate ($[SbF_6]^-$), hexafluoroarsenate ($[AsF_6]^-$), tetrachloroaluminate ($[AlCl_4]^-$), tetrabromoaluminate ($[AlBr_4]^-$), trichlorozincate ($[ZnCl_3]^-$), dichlorocuprates (I) and (II), carbonate ($CO_3^{2-}$), hydrogencarbonate ($HCO_3^-$), fluoride ($F^-$), triorganylsilanolate $R'_3SiO^-$, fluorosulfonate ($CF_3$—$SO_3$)—, sulfonate ($R'$—$SO_3$)⁻ and $[(R'$—$SO_2)_2N]^-$, where $R'$ is alkyl, cycloalkyl or aryl. R is preferably a linear or branched aliphatic or alicyclic alkyl radical containing from 1 to 12 carbon atoms or a $C_5$-$C_{18}$-aryl, $C_5$-$C_{18}$-aryl-$C_1$-$C_6$-alkyl or $C_1$-$C_6$-alkyl-$C_5$-$C_{18}$-aryl radical which may be substituted by halogen atoms.

$X^{n-}$ is particularly preferably selected from among $SO_4^{2-}$ and anions of organic monocarboxylic acids, preferably acetate.

The cation can be an acyclic or cyclic compound. The cation containing at least one quaternary sp²-hybridized nitrogen atom is preferably derived from imines, diazines (azo compounds), amidines, amidoximes, amidrazones, oximes, sulfimides, guanidines, phosphinimines, nitrogen-containing aromatic heterocycles, etc.

The cation is preferably derived from an aliphatic guanidine compound.

Preference is also given to the cation being derived from a heterocycloaliphatic compound which is preferably selected from among 4,5-dihydropyrazoles, 4,5-dihydrooxazoles, 4,5-dihydrothiazoles and 2-imidazolines.

Preference is also given to the cation being derived from a heterocycloaromatic compound which is preferably selected from among pyrroles, imidazoles, pyrazoles, indoles, carbazoles, benzimidazoles, indazoles, purines, 1,2,3-triazoles, 1,2,4-triazoles, benzotriazoles, oxazoles, isoxazoles, thiazoles, isothiazoles, pyridines, pyridazines, pyrimidines, pyrazines, quinolines, isoquinolines, phenanthridines, cinnolines, quinazolines, phthalazines, quinoxalines, 1,8-naphthyridines, pteridines, phenazines, acridines, 1,3,5-triazines, 1,2,4-triazines, benzotriazines and tetrazines.

Furthermore, it has surprisingly been found that compounds which contain at least one double-bonded nitrogen atom and are additionally capable of delocalizing a positive charge on this nitrogen atom can particularly advantageously be quaternized by means of dialkyl sulfates with participation of both alkyl groups.

Preference is therefore given to a process for preparing compounds of the general formula II

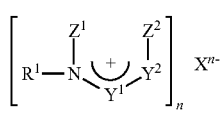

(II)

where
$R^1$ is $C_1$-$C_{10}$-alkyl,
$Y^1$ and $Y^2$ are selected independently from among heteroatoms and heteroatom-containing groups which each have a free electron pair and groups $CR^2$ in which the carbon atom is sp²-hybridized and $R^2$ is hydrogen or an organyl radical,
$Z^1$ and $Z^2$ are each, independently of one another, a single- or double-bonded organyl radical, where $Z^1$ and $Z^2$ may also together form a bridging group having from 2 to 5 atoms between the flanking bonds,
$X^{n-}$ is an anion which is preferably not Cl⁻, Br⁻, I⁻ or monoalkylsulfate, and
n is an integer from 1 to 3,
where the group $NR^1$—$Y^1$—$Y^2$ and, if appropriate, also $Z^1$ and/or $Z^2$ are part of a delocalized π electron system,
wherein
a) a compound of the general formula II.1

(II.1)

where $Y^1$, $Y^2$, $Z^1$ and $Z^2$ are as defined above, is reacted with a dialkyl sulfate $(R^1)_2SO_4$, where $R^1$ is $C_1$-$C_{10}$-alkyl, at elevated temperature with participation of both alkyl groups of the dialkyl sulfate to form a compound of the formula II in which $X^{n-}$ is a sulfate anion, and
b) if appropriate, the sulfate anion is exchanged for a different anion.

The cations of the compounds of the general formula II are capable of delocalization of the positive charge of the alkylated nitrogen atom over at least part of the remaining molecule.

The radical $R^1$ in the compounds of the formulae II and II.1 is preferably $C_1$-$C_4$-alkyl and in particular methyl or ethyl.

The values of y are integers from 1 to 240, preferably integers from 3 to 120.

In the compounds of the formulae II and II.1, the groups $Y^1$ and $Y^2$ are preferably selected independently from among O, S, $CR^2$, $NR^3$ and $PR^4$, where $R^2$, $R^3$ and $R^4$ are each, independently of one another, hydrogen, alkyl, cycloalkyl, heterocycloalkyl, aryl, hetaryl, $COOR^a$, $COO^-M^+$, $SO_3R^a$, $SO_3^-M^+$, sulfonamide, $NE^1E^2$, $(NE^1E^2E^3)^+A^-$, $OR^a$, $SR^a$, $(CHR^bCH_2O)_yR^a$, $(CH_2O)_yR^8$, $(CH_2CH_2NE^1)_yR^a$, alkylaminocarbonyl, dialkylaminocarbonyl, alkylcarbonylamino, halogen, nitro, acyl or cyano, where
the radicals $R^a$ are identical or different and are selected from among hydrogen, alkyl, cycloalkyl, aryl, heterocycloalkyl and hetaryl,
$E^1$, $E^2$, $E^3$ are identical or different radicals selected from among hydrogen, alkyl, cycloalkyl, aryl and hetaryl,
$R^b$ is hydrogen, methyl or ethyl,
$M^+$ is a cation equivalent,
$A^-$ is an anion equivalent and
y is an integer from 1 to 250.

In a preferred embodiment, one of the groups $Y^1$ and $Y^2$ is a group of the formula $CR^2$ and the other is selected from among O, S, $CR^2$, $NR^3$ and $PR^4$. Particular preference is then given to one of the groups $Y^1$ and $Y^2$ being a group of the formula $CR^2$ and the other being selected from among O, S and $NR^3$. In particular, the group $Y^1$ is a group of the formula $CR^2$.

$R^2$ is preferably hydrogen. Preference is also given to $R^2$ being a group of the formula $OR^c$, $SR^c$ or $NR^cR^d$, where $R^c$ and $R^d$ are identical or different radicals selected from among hydrogen, alkyl, cycloalkyl, heterocycloalkyl, aryl and hetaryl. Such groups $R^2$ allow the positive charge of the cation of the compounds I to be additionally stabilized by delocalization.

$R^3$ and $R^4$ are preferably selected from among hydrogen, alkyl, preferably $C_1$-$C_{10}$-alkyl such as methyl, ethyl, propyl, isopropyl, n-butyl and tert-butyl, cycloalkyl, preferably $C_5$-$C_7$-cycloalkyl such as cyclopentyl and cyclohexyl, and aryl, in particular phenyl.

In a first preferred embodiment, $Z^1$ and $Z^2$ are not connected to one another by a bridge. In this case, $Z^1$ and $Z^2$ are preferably selected independently from among alkyl, cycloalkyl, heterocycloalkyl, aryl and hetaryl, as defined above.

When $Z^1$ and $Z^2$ are not connected to one another by a bridge, the cations of the compounds of the formula II are preferably guanidinium ions of the formula

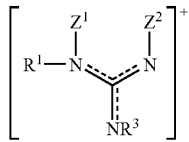

where $R^1$, $R^3$, $Z^1$ and $Z^2$ are as defined above.

In a preferred embodiment, $Z^1$ and $Z^2$ are joined to one another by a bridge. In this case, $Z^1$ and $Z^2$ together with the group $NR^1$—$Y^1$—$Y^2$ to which they are bound preferably form a 5- to 8-membered heterocycle which may optionally be fused singly, doubly or triply to cycloalkyl, heterocycloalkyl, aryl and/or hetaryl groups, with the fused-on groups being unsubstituted or each being able to bear, independently of one another, one, two, three or four substituents. The substituents of the fused-on groups are preferably selected from among alkyl, alkoxy, amino, polyalkylene oxide, polyalkylenimine, halogen, nitro, cyano, sulfonate and carboxylate.

$Z^1$ and $Z^2$ preferably together form a bridging group having two or three atoms between the flanking bonds, which are selected from among optionally substituted heteroatoms and sp$^2$-hybridized carbon atoms, with the bridging group together with the group $NR^1$—$Y^1$—$Y^2$ forming a delocalized π electron system.

The cation of the compounds of the formula I is preferably derived from a heterocycloaromatic group which is preferably selected from among pyrrole, imidazole, pyrazole, 1,2,3-triazole, 1,2,4-triazole, indole, oxazole, thiazole, pyridine, pyrimidine, 1,3,5-triazine and 1,2,4-triazine groups.

The compound of the formula II is particularly preferably selected from among compounds of the formulae II.a to II.e

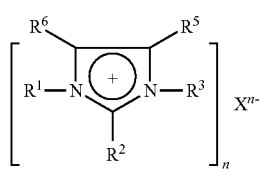
(II.a)

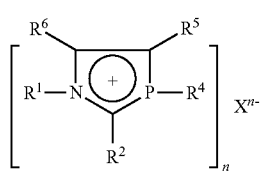
(II.b)

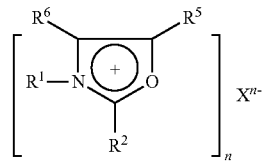
(II.c)

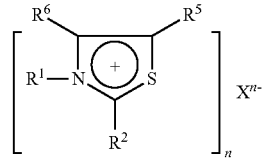
(II.d)

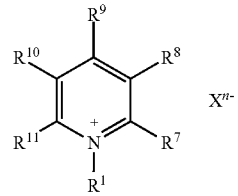
(II.e)

where $X^{n-}$ is an anion which is preferably not Cl$^-$, Br$^-$, I$^-$ nor monoalkylsulfate, and n is an integer from 1 to 3, $R^1$ is $C_1$-$C_{10}$-alkyl, and $R^2$, $R^3$, $R^4$, $R^5$, $R^6$, $R^7$, $R^8$, $R^9$, $R^{10}$ and $R^{11}$ are each, independently of one another, hydrogen, alkyl, cycloalkyl, heterocycloalkyl, aryl, hetaryl, COOR$^a$, COO$^-$M$^+$, SO$_3$R$^a$, SO$_3^-$M$^+$, sulfonamide, NE$^1$E$^2$, (NE$^1$E$^2$E$^3$)$^+$A$^-$, OR$^a$, SR$^a$, (CHR$^b$CH$_2$O)$_y$R$^a$, (CH$_2$O)$_y$R$^a$, (CH$_2$CH$_2$NE$^1$)$_y$R$^a$, alkylaminocarbonyl, dialkylaminocarbonyl, alkylcarbonylamino, halogen, nitro, acyl or cyano, where the radicals R$^a$ are identical or different and are selected from among hydrogen, alkyl, cycloalkyl, aryl and hetaryl, E$^1$, E$^2$, E$^3$ are identical or different radicals selected from among hydrogen, alkyl, cycloalkyl, aryl and hetaryl, R$^b$ is hydrogen, methyl or ethyl, M$^+$ is a cation equivalent, A$^-$ is an anion equivalent and y is an integer from 1 to 250.

In the compounds of the formula II.a to II.d, preference is given to the radicals $R^2$, $R^5$ and $R^6$ each being, independently of one another, hydrogen or alkyl, in particular $C_1$-$C_6$-alkyl such as methyl, ethyl, propyl, isopropyl, n-butyl and tert-butyl.

In the compounds of the formula II.e, preference is given to the radicals $R^7$, $R^8$, $R^9$, $R^{10}$ and $R^{11}$ each being, independently of one another, hydrogen or alkyl, in particular $C_1$-$C_6$-alkyl such as methyl, ethyl, propyl, isopropyl, n-butyl and tert-butyl. It is preferred that one of the radicals $R^7$, $R^8$, $R^9$, $R^{10}$ and $R^{11}$ is alkyl, especially methyl, and the others are hydrogen.

For the preparation according to the invention of ionic compounds comprising at least one cation containing a quaternary sp$^2$-hybridized nitrogen atom, a compound containing a double-bonded nitrogen atom is reacted with a dialkyl sulfate with participation of both alkyl groups of the dialkyl sulfate in a first reaction step a) to give an ionic compound containing sulfate anions and, if appropriate, the ionic compound obtained in step a) is subsequently subjected to an anion exchange in a step b).

According to the invention, the reaction in step a) is carried out at an elevated temperature, i.e. at a temperature above ambient temperature. The temperature in step a) is preferably at least 60° C., particularly preferably at least 80° C. The reaction in step a) is preferably carried out at a temperature in the range from 100 to 220° C., particularly preferably from 120 to 200° C.

The reaction in step a) can be carried out under ambient pressure or under reduced pressure or elevated pressure. The reaction is preferably carried out under the autogenous pressure of the reaction mixture under the reaction conditions. When volatile amines are used, the pressure in the reaction in step a) is generally at least 1.5 bar, in particular at least 2 bar. If desired, the pressure in the reaction in step a) can be up to 300 bar. Suitable pressure-rated reactors are known to those skilled in the art and are described, for example, in Ullmanns Enzyklopadie der technischen Chemie, volume 1, 3rd edition, 1951, p. 769 ff. In general, an autoclave is used for the process of the invention, and this can, if desired, be provided with a stirrer and/or an interior lining.

The molar ratio of the compound which contains a double-bonded nitrogen atom and is to be alkylated to the dialkyl sulfate is preferably at least 2:1. The molar ratio of the compound to be alkylated to the dialkyl sulfate is particularly preferably in a range from 1.8:1 to 10:1, in particular from 2.05:1 to 5:1, especially from 2.1:1 to 3:1.

The reaction of the compound to be alkylated with the dialkyl sulfate can be carried out in bulk or in the presence of a solvent which is inert under the reaction conditions. Suitable solvents are, for example, water, water-miscible solvents, for example alcohols such as methanol and ethanol, and mixtures thereof. Preference is given to using water or a solvent mixture comprising at least 30% by volume, preferably at least 50% by volume, in particular at least 80% by volume, of water as solvent.

The dialkyl sulfates used in step a) are preferably di-$C_1$-$C_{10}$-alkyl sulfates and, in particular, di-$C_1$-$C_6$-alkyl sulfates such as dimethyl sulfate, diethyl sulfate, di-n-propyl sulfate, diisopropyl sulfate, di-n-butyl sulfate, diisobutyl sulfate, di-tert-butyl sulfate, di-n-pentyl sulfate, diisopentyl sulfate, dineopentyl sulfate and di-n-hexyl sulfate. Particular preference is given to using dimethyl sulfate and diethyl sulfate.

If desired, the reaction in step a) can be carried out in the presence of at least one inert gas. Suitable inert gases are, for example, nitrogen, helium and argon.

The reaction step a) can be carried out continuously or batchwise.

The sulfate salt can be isolated from the reaction mixture obtained in step a) by customary methods known to those skilled in the art. If a solvent has been used for the reaction in step a), this can be removed by evaporation, preferably under reduced pressure. Since the ionic compounds obtained are nonvolatile, the pressure range employed is generally not critical. If virtually complete removal of the solvent is desired, it is possible to employ, for example, a fine vacuum of from $10^1$ to $10^{-1}$ Pa or a high vacuum of from $10^{-1}$ to $10^{-5}$ Pa. To generate the pressure, it is possible to use customary vacuum pumps such as liquid jet vacuum pumps, rotary vane and rotary piston vacuum pumps, diaphragm vacuum pumps, diffusion pumps, etc. The removal of the solvent can also be carried out at an elevated temperature of up to 150° C., preferably up to 100° C.

If the alkylation reaction in step a) is followed by an anion exchange reaction in step b), the sulfate salt obtained in step a) can be isolated by the methods described above. This applies especially when the reaction in step b) is to be carried out in a solvent different from that used in the alkylation step a). In a further embodiment, the reaction mixture obtained in step a) is used for the reaction in step b) without prior isolation.

The exchange of the sulfate anion is step b) can be effected by transprotonation with $H_2SO_4$, reaction with a metal salt, ion exchange chromatography or a combination of these measures.

In a first embodiment, the ionic compound based on sulfate anions which is obtained in step a) of the process of the invention is reacted with sulfuric acid so as to transfer protons and give the corresponding hydrogensulfates ($X^{n-}=HSO_4^-$). The transprotonation is preferably carried out using 100% strength $H_2SO_4$. The molar ratio of $H_2SO_4$ to $SO_4^{2-}$ is preferably $\geq$ 1:1 and is, for example, in a range from 1:1 to 2:1. The resulting ionic compounds based on hydrogensulfate anions are generally suitable both as ionic liquids and as intermediates for further anion exchange.

In a further embodiment, the anion exchange in step b) is effected by reaction with a metal salt. This reaction is preferably carried out in a solvent from which the metal sulfate formed from the metal of the metal salt and the sulfate anion crystallizes out. The above-described hydrogen sulfates can also be used for this variant of the anion exchange. The cation of the meal salt is preferably an alkali metal, alkaline earth metal, lead or silver ion. The anion of the metal salt is selected from among the abovementioned anions $X^{n-}$, in particular anions other than Cl$^-$, Br$^-$, I$^-$ and monoalkylsulfate. In a suitable procedure, a solution of the metal salt is brought into contact with a solution of the ionic compound. Suitable solvents are, for example, water, water-miscible solvents, for example alcohols such as methanol and ethanol, and mixtures thereof. The reaction temperature is preferably in a range from $-10$ to 100° C., in particular from 0 to 80° C.

In a further embodiment, the anion exchange in step b) is effected by ion exchange chromatography. The basic ion exchangers which are known to those skilled in the art and comprise at least one base immobilized on a solid phase are in principle suitable for this purpose. The solid phase of these basic ion exchangers comprises, for example, a polymer matrix. Such matrices include, for example, polystyrene matrices comprising styrene together with at least one crosslinking monomer, e.g. divinylbenzene, and also, if appropriate, further comonomers in copolymerized form. Also suitable are polyacrylic matrices which are obtained by polymerization of at least one (meth)acrylate, at least one crosslinking monomer and, if appropriate, further comonomers. Suitable polymer matrices are also phenol-formaldehyde resins and polyalkylamine resins obtained, for example, by condensation of polyamines with epichlorohydrin.

The anchor groups (whose loosely bound counterions can be replaced by ions bearing a charge of the same sign) bound directly or via a spacer group to the solid phase are preferably selected from among nitrogen-containing groups, preferably tertiary and quaternary amino groups.

Suitable functional groups are, for example (in order of decreasing basicity):
—$CH_2N^+(CH_3)_3$ OH e.g. Duolite A 101
—$CH_2N^+(CH_3)_2CH_2CH_2OH$ OH$^-$ e.g. Duolite A 102
—$CH_2N(CH_3)_2$ e.g. Amberlite IRA 67
—$CH_2NHCH_3$
—$CH_2NH_2$ e.g. Duolite A 365

Both strongly basic and weakly basic ion exchangers are suitable for the process of the invention. Among the weakly basic ion exchangers, preference is given to those bearing tertiary amino groups. Strongly basic ion exchangers generally have quaternary ammonium groups as anchor groups. Commercially available ion exchangers suitable for the process of the invention include, for example, Amberlyst® A21 (dimethylamino-functionalized, weakly basic) and Amberlyst® A27 (quaternary ammonium groups, strongly basic). For the ion exchange, the ion exchangers are firstly loaded with the desired anions $X^{n-}$ and subsequently brought into contact with the ionic compounds based on sulfate anions (or hydrogensulfate anions).

The process of the invention makes it possible for the first time to prepare compounds of the general formula b $B^{m+}xX^{n}$ (I), as defined above, which are free of $Cl^-$, $Br^-$, $I^-$ and at the same time free of monoalkylsulfate anions. To prepare compounds of the formula I having an extremely low residual content of halide ions, the reaction in steps a) and b) is preferably carried out with the exclusion of halide ions and of materials which release these. Thus, reagents, solvents, inert gases, etc., which are substantially free of halide ions can be used for the reaction. Such components are commercially available or can be prepared by customary purification methods known to those skilled in the art. These include, for example, adsorption, filtration and ion exchange processes. If desired, the apparatuses used in steps a) and b) can also be freed of halide ions before use, e.g. by rinsing with halide-free solvents. The process of the invention makes it possible to prepare compounds of the general formula I in which $X^{n-}$ is $SO_4^{2-}$ and the total content of halide ions is not more than 100 ppm, preferably not more than 10 ppm and in particular not more than 1 ppm. Furthermore, it is possible to obtain compounds which have a total content of monoalkylsulfate anions of not more than 100 ppm, preferably not more than 10 ppm and in particular not more than 1 ppm.

The invention further provides for the use of the above-mentioned halide-free and monoalkylsulfate-free salts as intermediates for preparing ionic liquids and as components and for the preparation of components for pharmaceutical preparations. These include, for example, the salts of clonidine:

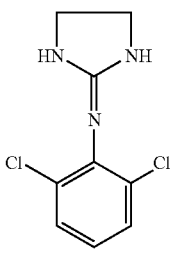

The invention is illustrated by the following nonrestrictive examples.

EXAMPLES

Example 1

Preparation of 1-butyl-3-methylimidazolium sulfate by reaction in water 100 ml of distilled water and 12.6 g (0.1 mol) of dimethyl sulfate were placed in a 250 ml flask provided with a dropping funnel and magnetic stirrer, and 27.3 g (0.22 mol) of butylimidazole were added dropwise while stirring, with the internal temperature being kept at 23-25° C. by cooling in ice. The reaction mixture was subsequently transferred to a 300 ml stirring autoclave and the autoclave was heated at 180° C. for 6 hours while stirring. During this time, the internal pressure rose to 8.1 bar. After cooling and depressurization, the crude output was concentrated on a rotary evaporator and the residue obtained was dried at 60° C. in an oil pump vacuum, giving an oily substance. This was stirred with 450 ml of acetone at room temperature for 3 hours and subsequently allowed to stand overnight at room temperature. The acetone was subsequently drawn off under a nitrogen atmosphere, the resulting solid was washed again with 100 ml of acetone and subsequently dried. This gave 34.05 g (92.3% of theory) of product.

Example 2

Preparation of 1-butyl-3-methylimidazolium sulfate in methanol

A mixture of 95 g of methanol and 5 g of water and 12.6 g (0.1 mol) of dimethyl sulfate was placed in a 250 ml flask provided with a dropping funnel and magnetic stirrer, and 27.3 g (0.22 mol) of butylimidazole were added dropwise while stirring, with the internal temperature being kept at 23-25° C. by cooling in ice. The reaction mixture was subsequently transferred to a 300 ml stirring autoclave and the autoclave was heated at 180° C. for 6 hours while stirring. During this time, the internal pressure rose to 8.1 bar. After cooling and depressurization, the crude output was concentrated on a rotary evaporator and the residue obtained was dried at 60° C. in an oil pump vacuum, giving an oily substance. This was stirred with 450 ml of acetone at room temperature for 3 hours and subsequently allowed to stand overnight at room temperature. The acetone was subsequently drawn off under a nitrogen atmosphere, the resulting solid was washed again with 100 ml of acetone and subsequently dried. This gave 33.7 g (90% of theory) of product.

Example 3

Preparation of 1-methyl-3-ethylimidazolium sulfate in water 15.4 g (0.1 mol) of diethyl sulfate were placed in a 250 ml stirred flask provided with a dropping funnel and magnetic stirrer, and 18.04 g (0.22 mol) of methylimidazole were added dropwise over a period of 15 minutes, with the internal temperature being kept at 23-25° C. by cooling in ice. 100 ml of distilled water were subsequently added dropwise over a period of 10 minutes, likewise with cooling in ice, and the reaction mixture was stirred at 25° C. for 3 hours. The reaction mixture was subsequently transferred to a 300 ml stirring autoclave and the autoclave was heated at 180° C. for 6 hours while stirring, with the internal pressure rising to 9.2 bar. After cooling and depressurization, the crude output is concentrated on a rotary evaporator and the residue obtained is dried at 60° C. in an oil pump vacuum. This gives an oily substance which is stirred with 450 ml of acetone at room temperature for 3 hours and subsequently allowed to stand overnight at room temperature. The acetone is subsequently drawn off under a nitrogen atmosphere and the resulting product is washed and dried. This gave 30.65 g of product.

Example 4

Preparation of 1-butyl-3-methylimidazolium acetate 31.5 g (0.1 mol) of barium hydroxide (octahydrate), 12 g (0.2 mol) of acetic acid and 174 g of water were placed in a 1 l stirred flask equipped with a dropping funnel and the mixture was heated to 40° C. A solution of 37.7 g (0.1 mol) of the 1-butyl-3-methylimidazolium sulfate obtained in Example 1 in 339.3 g of water was added dropwise from the dropping funnel over a period of 30 minutes. Immediately after commencement of the addition, a snow-white finely pulverulent precipitate of barium sulfate was formed. After the addition was complete, the reaction mixture was stirred for another 1.5 hours at 40° C., cooled and the precipitate was filtered off with suction via a D4 suction filter. The resulting solution was concentrated on a rotary evaporator and the residue obtained was dried at 60° C. in an oil pump vacuum. This gave 35.2 g (81% of theory) of product.

Example 5

Preparation of 1-butyl-3-methylimidazolium tetraphenylborate

A solution of 9.35 g (0.025 mol) of the 1-butyl-3-methylimidazolium sulfate obtained in Example 1 in 15.9 g of methanol was placed under a nitrogen atmosphere in a 100 ml stirred flask equipped with a dropping funnel. A solution of 17 g of sodium tetraphenylborate in 27.5 g of methanol was slowly added dropwise from the dropping funnel. Immediately after commencement of the addition, a precipitate of sodium sulfate was formed. After the addition was complete, the reaction mixture was stirred for another 2 hours at 30° C., cooled and the precipitate was filtered off. The precipitate is washed with 20 ml of methanol. The combined solutions are concentrated, resulting in precipitation of a white solid which is isolated and dried. This gives 21.2 g (92% of theory) of 1-butyl-3-methylimidazolium tetraphenylborate.

Example 6

Preparation of 1-methyl-3-ethylimidazolium trimethylsilanolate

A solution of 40 g (0.125 mol) of the 1-methyl-3-ethylimidazolium sulfate obtained in Example 3 in 40 g of methanol was placed under a nitrogen atmosphere in a 250 ml stirred flask equipped with a dropping funnel. A solution of 28.12 g (0.25 mol) of sodium trimethylsilanolate in 60.2 g of methanol was slowly added dropwise from the dropping funnel. Immediately after commencement of the addition, a precipitate of sodium sulfate was formed. After the addition was complete, the reaction mixture was stirred for another 2 hours at 30° C., cooled and the precipitate was filtered off. The precipitate is washed with 20 ml of methanol. The combined solutions are concentrated, resulting in an oily product which is dried. This gives 29.8 g (58.7% of theory) of 1-methyl-3-ethylimidazolium trimethylsilanolate.

Example 7

Preparation of 1-butyl-3-methylimidazolium acetate

A solution of 60.18 g (0.16 mol) of the 1-butyl-3-methylimidazolium sulfate obtained in Example 1 in 56 g of methanol was placed under a nitrogen atmosphere in a 500 ml stirred flask equipped with a dropping funnel. A solution of 26.24 g of sodium acetate in 183 g of methanol was added dropwise from the dropping funnel over a period of one hour. Immediately after commencement of the addition, a precipitate of sodium sulfate was formed. After the addition was complete, the reaction mixture was stirred for another 2 hours at 30° C., cooled and the precipitate was filtered off. The precipitate is washed with 20 ml of methanol. The combined solutions are concentrated, leaving a light-yellow liquid which is dried under reduced pressure. This gives 53.9 g (85% of theory) of 1-butyl-3-methylimidazolium acetate.

Example 8

Preparation of 1-methyl-3-ethylimidazolium acetate 149.8 g (0.72 mol) of 1-methyl-3-ethylimidazolium hydrogensulfate are dissolved in 600 ml of water, and 226.8 g (0.72 mol) of $Ba(OH)_2$ (octahydrate) are subsequently added in portions over a period of 30 minutes. The temperature is increased to 60° C. and the reaction mixture is stirred for 2 hours at this temperature. It is allowed to cool overnight and the precipitated $BaSO_4$ is filtered off using Celite as filter aid. After addition of 43.5 g (0.72 mol) of glacial acetic acid, the water is removed on a rotary evaporator and the oil which remains is extracted with ethyl acetate. To remove residual water, the oil is admixed with n-butanol and the n-butanol is subsequently distilled off under reduced pressure. This gives 108.3 g (0.636 mol) of 1-methyl-3-ethylimidazolium acetate (yield: 88% based on 1-methyl-3-ethylimidazolium hydrogensulfate). The chloride content is 4 ppm.

Example 9

Preparation of 1-methyl-3-ethylimidazolium acetate 226.8 g (0.72 mol) of $Ba(OH)_2$ (octahydrate) are suspended in 600 g of water. The suspension is heated to 80° C., resulting in the barium salt melting and forming an aqueous emulsion. 149.8 g (0.72 mol) of 1-methyl-3-ethylimidazolium hydrogensulfate are added dropwise to this emulsion, with the temperature rising to 100° C. Despite the barium sulfate which precipitates, the suspension remains readily stirrable. The reaction mixture is stirred for another 2 hours at 80° C., cooled and the precipitated $BaSO_4$ is filtered off using Celite as filter aid. After addition of 43.5 g (0.72 mol) of glacial acetic acid, the water is removed on a rotary evaporator and the oil which remains is extracted with ethyl acetate. Drying under reduced pressure gives 113.3 g (0.67 mol) of 1-methyl-3-ethylimidazolium acetate (yield: 92%). The chloride content is 4 ppm.

Example 10

Preparation of 1-methyl-3-ethylimidazolium dihydrogenphosphate 208 g (1.0 mol) of 1-methyl-3-ethylimidazolium hydrogensulfate are dissolved in 600 ml of water, and 315.3 g (1.0 mol) of $Ba(OH)_2$ (octahydrate) are subsequently added in portions over a period of 30 minutes. The temperature is increased to 60° C. and the reaction mixture is stirred for 2 hours at this temperature. It is allowed to cool overnight and the precipitated $BaSO_4$ is filtered off using Celite as filter aid. After addition of 115.3 g (1.0 mol) of 85% strength phosphoric acid, the water is removed on a rotary evaporator. This gives a white solid (202.8 g, 0.975 mol) having a melting point of 140° C. (yield: 98% based on 1-methyl-3-ethylimidazolium hydrogensulfate). The chloride content is 4 ppm.

Example 11

Preparation of 1-methyl-3-ethylimidazolium dihydrogenborate 631 g (2.0 mol) of $Ba(OH)_2$ (octahydrate) and 123.6 g (2.0 mol) of boric acid are suspended in 500 ml of water at 60° C.

208 g (1.0 mol) of 1-methyl-3-ethylimidazolium hydrogensulfate are added dropwise to this mixture over a period of 60 minutes. After addition of a further 500 ml of water, the precipitated $BaSO_4$ is filtered off using Celite as filter aid and washed with water. After addition of n-butanol, the water is removed on a rotary evaporator and the residue is dried under reduced pressure to give 247.2 g (1.44 mol) of 1-methyl-3-ethylimidazolium dihydrogenborate (yield: 72%, melting point: 40° C.).

The invention claimed is:

1. A process for preparing an ionic compound comprising at least one cation containing a quaternary $sp^2$-hybridized nitrogen atom, which comprises
   a) reacting a compound comprising an imidazole ring with a dialkyl sulfate with participation of both alkyl groups of the dialkyl sulfate to give an ionic compound containing sulfate anions, and
   b) if appropriate, subjecting the ionic compound obtained in step a) to an anion exchange.

2. The process according to claim 1, wherein the ionic compound obtained comprises at least one anion $X^{n-}$ in which n is an integer corresponding to the valence of the anion and which is selected from among $SO_4^{2-}$, $HSO_4^-$, $NO_2^-$, $NO_3^-$, $CN^-$, $OCN^-$, $NCO^-$, $SCN^-$, $NCS^-$, $PO_4^{3-}$, $HPO_4^{2-}$, $H_2PO_4^-$, $H_2PO_3^-$, $HPO_3^{2-}$, $BO_3^{3-}$, $(BO_2)_3^{3-}$, $[BF_4]^-$, $[BCl_4]^-$, $[B(C_6H_5)_4]^-$, $[PF_6]^-$, $[SbF_6]^-$, $[AsF_6]^-$, $[AlCl_4]^-$, $[AlBr_4]^-$, $[ZnCl_3]^-$, dichlorocuprates (I) and (II), $CO_3^{2-}$, $HCO_3^-$, $F^-$, $(CF_3-SO_3)^-$, $R'_3SiO^-$, $R'-SO_3^-$ and $[(R'-SO_2)_2N]^-$, where R' is alkyl, cycloalkyl or aryl.

3. The process according to claim 1, wherein the reaction in step a) is carried out at a temperature of at least 60° C.

4. The process according to claim 1, wherein the molar ratio of the compound comprising an imidazole ring to the dialkyl sulfate is at least 2:1.

5. The process according to claim 1, wherein the reaction in step a) is carried out in an organic solvent, in water or in a mixture thereof.

6. The process according to claim 5, wherein the solvent comprises at least 30% by volume of water.

7. The process according to claim 1, wherein the reaction in step a) is carried out in the presence of an inert gas.

8. The process according to claim 1, wherein the dialkyl sulfate is dimethyl sulfate or diethyl sulfate.

9. The process according to claim 1, wherein the process steps a) and b) are carried out in the absence of halide ions.

10. The process according to claim 1, wherein the exchange of the sulfate anion in step b) is effected by transprotonation with $H_2SO_4$, reaction with a metal salt, ion exchange chromatography or a combination thereof.

11. The process according to claim 10, wherein the reaction with the metal salt is carried out in a solvent from which a metal sulfate formed from the metal of the metal salt and the sulfate anion crystallizes out.

12. The process according to claim 1, wherein the reaction in step a) is carried out at a temperature in the range from 100 to 220° C.

* * * * *